United States Patent
Rao et al.

(10) Patent No.: US 9,676,803 B2
(45) Date of Patent: Jun. 13, 2017

(54) EFFICIENT PROCESS FOR SEPARATION OF DIASTEREOMERS OF 9-[(R)-2-[[(R,S)-[[(S)-1-(ISOPROPOXYCARBONYL)ETHYL]AMINO]-PHENOXYPHOSPHINYL]METHOXY]PROPYL]ADENINE

(71) Applicant: Cipla Limited, Mumbai (IN)

(72) Inventors: Dharmaraj Ramachandra Rao, Thane (IN); Ashwini Amol Sawant, Mumbai (IN); Nayan Shivalkar, Thane (IN); Nitin Thakur, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 14/896,313

(22) PCT Filed: Jun. 6, 2014

(86) PCT No.: PCT/GB2014/051752
§ 371 (c)(1),
(2) Date: Dec. 4, 2015

(87) PCT Pub. No.: WO2014/195724
PCT Pub. Date: Dec. 11, 2014

(65) Prior Publication Data
US 2016/0122373 A1     May 5, 2016

(30) Foreign Application Priority Data
Jun. 7, 2013 (IN) .......................... 1967/MUM/2013

(51) Int. Cl.
*C07F 9/6561* (2006.01)
(52) U.S. Cl.
CPC ........ *C07F 9/65616* (2013.01); *C07F 9/6561* (2013.01)

(58) Field of Classification Search
None
See application file for complete search history.

(56) References Cited

FOREIGN PATENT DOCUMENTS

| IN | 1967/MUM/2013 | 6/2013 |
|---|---|---|
| WO | 0208241 A2 | 1/2002 |
| WO | 2013052094 A2 | 4/2013 |
| WO | 2014195724 A1 | 12/2014 |

OTHER PUBLICATIONS

Faigl, Ference. Tetrahedron: Asymmetry 19 (2008) 519-536.*
MSU Organic Chemistry. Ionization Constants of B—H+ Onium Acids. Michigan State University: Organic Chemistry. (2010) Web< <https://web.archive.org/web/20100702174211/http://www.cem.msu.edu/~reusch/OrgPage/basicity.htm>.*
Foreign communication from a related counterpart application—International Search Report and Written Opinion, PCT/GB2014/051752, Sep. 9, 2014, 10 pages.
Foreign communication from a related counterpart application—International Preliminary Report on Patentability, PCT/GB2014/051752, Dec. 8, 2015, 8 pages.

* cited by examiner

*Primary Examiner* — Golam M M Shameem
*Assistant Examiner* — Laura Daniel
(74) *Attorney, Agent, or Firm* — Conley Rose, P.C.; Rodney B. Carroll

(57) ABSTRACT

The present invention relates to an efficient process for the separation of diastereomers of 9-[(R)-2-[[(R,S)-[[(S)-1-(Isopropoxycarbonyl)ethyl]amino]-phenoxyphosphinyl]methoxy]propyl]adenine and to a process for preparing 9-[(R)-2-[[(R)-[[(S)-1-(Isopropoxycarbonyl)ethyl]amino]phenoxyphosphinyl]methoxy]propyl]adenine and 9-[(R)-2-[[(S)-[[(S)-1-(Isopropoxycarbonyl)ethyl]amino]phenoxyphosphinyl]methoxy]propyl]adenine.

24 Claims, No Drawings

EFFICIENT PROCESS FOR SEPARATION OF DIASTEREOMERS OF 9-[(R)-2-[[(R,S)-[[(S)-1-(ISOPROPOXY CARBONYL)ETHYL]AMINO]-PHENOXYPHOSPHINYL]METHOXY] PROPYL]ADENINE

CROSS-REFERENCE TO RELATED APPLICATIONS

This application is a filing under 35 U.S.C. 371 of International Application No. PCT/GB2014/051752 filed Jun. 6, 2014, entitled "An Efficient Process For Separation Of Diastereomers Of 9-[(R)-2-[[(R,S)-[[(S)-1-(Isopropoxycarbonyl)Ethyl]Amino]-Phenoxyphosphinyl] Methoxy]Propyl]Adenine," which claims priority to Indian Patent Application No. 1967/MUM/2013 filed Jun. 7, 2013, which applications are incorporated by reference herein in their entirety.

FIELD OF INVENTION

The present invention relates to an efficient process for the separation of diastereomers of 9-[(R)-2-[[(R,S)-[[(S)-1-(Isopropoxycarbonyl)ethyl]amino]-phenoxyphosphinyl] methoxy]propyl]adenine and to a process for preparing 9-[(R)-2-[[(R)-[[(S)-1-(Isopropoxycarbonyl)ethyl]amino] phenoxyphosphinyl]methoxy]propyl]adenine and 9-[(R)-2-[[(S)-[[(S)-1-(Isopropoxycarbonyl)ethyl]amino]phenoxyphosphinyl]methoxy]propyl]adenine.

BACKGROUND AND PRIOR ART

9-[(R)-2-[[(R,S)-[[(S)-1-(Isopropoxycarbonyl)ethyl] amino]-phenoxyphosphinyl]methoxy]propyl]adenine, an isopropylalaninyl monoamidate phenyl monoester prodrug of tenofovir, is a diastereomeric mixture. It was first disclosed in PCT Patent Application, Publication Number WO200208241. The process for separation of the diastereomers of 9-[(R)-2-[[(R,S)-[[(S)-1-(Isopropoxycarbonyl) ethyl]amino]-phenoxyphosphinyl]methoxy]propyl]adenine disclosed in WO200208241 involves the use of chromatography or crystallization techniques. The chromatography techniques described are batch elution chromatography, simulated bed chromatography and C18 Reverse phase high performance liquid chromatography.

OBJECT OF THE INVENTION

The main object of the present invention is to provide a simple, efficient and industrial feasible process for the separation of diastereomers of 9-[(R)-2-[[(R,S)-[[(S)-1-(Isopropoxycarbonyl)ethyl]amino]phenoxyphosphinyl] methoxy]propyl]adenine.

Another object of the present invention is to provide a process for the preparation of 9-[(R)-2-[[(R)-[[(S)-1-(Isopropoxycarbonyl)ethyl]amino]phenoxyphosphinyl] methoxy]propyl]adenine and 9-[(R)-2-[[(S)-[[(S)-1-(Isopropoxycarbonyl)ethyl]amino]phenoxyphosphinyl] methoxy]propyl]adenine.

As used herein, "9-[(R)-2-[[(R,S)-[[(S)-1-(Isopropoxycarbonyl)ethyl]amino]phenoxyphosphinyl]methoxy]propyl] adenine" refers collectively to 9-[(R)-2-[[(R)-[[(S)-1-(Isopropoxycarbonyl)ethyl]amino]phenoxyphosphinyl] methoxy]propyl]adenine and 9-[(R)-2-[[(S)-[[(S)-1-(Isopropoxycarbonyl)ethyl]amino]phenoxyphosphinyl] methoxy]propyl]adenine. The diastereomers may be racemic (50:50) or may collectively contain a higher proportion of one diastereomer relative to the other.

DETAILED DESCRIPTION OF THE INVENTION

The invention will now be described in detail in connection with certain various embodiments, so that various aspects thereof may be more fully understood and appreciated.

It is known in the art that use of chromatographic techniques for the separation of diastereomers at the industrial scale requires a remarkable starting investment. Building the set-up for chromatography is an expensive process. Also, large volumes of solvent(s) are required for separation which not only increase the overall cost of the process, but also is environment unfriendly. Further, the separation of diastereomers by chromatography is a tedious and time-consuming process.

The inventors of the present invention have developed an efficient process that is cost-effective and industrially suitable process in comparison with the known methods.

In their attempt to prepare a simple and efficient method for separation of diastereomers of 9-[(R)-2-[[(R,S)-[[(S)-1-(Isopropoxycarbonyl)ethyl]amino]-phenoxyphosphinyl] methoxy]propyl]adenine, the present inventors have unexpectedly found that resolution by means of diastereomeric salt formation has very high success rate. Advantageously, pure diastereomers prepared according to the process of the present invention are obtained in less time than using known separation methods.

The process of present invention involves the use of a suitable resolving agent for resolution of diastereomers of 9-[(R)-2-[[(R,S)-[[(S)-1-(Isopropoxycarbonyl)ethyl] amino]-phenoxyphosphinyl]methoxy]propyl]adenine.

According to a first aspect of the present invention, there is provided a process for the separation of diastereomers of 9-[(R)-2-[[(R,S)-[[(S)-1-(Isopropoxycarbonyl)ethyl]amino] phenoxyphosphinyl]methoxy]propyl]adenine, comprising the steps (a-c) of:
   a. reacting phenyl((R)-1-(6-amino-9H-purin-9-yl)propan-2-yloxy)methyl phosphonochloridate with 2-aminopropionic acid isopropyl ester or the hydrochloride salt thereof and a suitable chiral organic acid to obtain a diastereomeric organic acid addition salt of 9-[(R)-2-[[(R,S)-[[(S)-1(Isopropoxycarbonyl)ethyl]amino]phenoxyphosphinyl]methoxy]propyl]adenine;
   b. crystallising a diastereomeric organic acid addition salt of 9-[(R)-2-[[(R,S)-[[(S)-1(Isopropoxycarbonyl)ethyl] amino]phenoxyphosphinyl]methoxy]propyl]adenine from the reaction mixture of step (a) using a suitable solvent or mixture of solvents; and
   c. treating a diastereomeric organic acid addition salt of 9-[(R)-2-[[(R,S)-[[(S)-1(Isopropoxycarbonyl)ethyl] amino]phenoxyphosphinyl]methoxy]propyl]adenine from the reaction mixture of step (b) with a suitable base; and optionally thereafter performing one or more of the following steps:
   d. isolating the product so formed; and/or
   e. increasing the diastereomeric purity of the product so formed.

According to a second aspect of the present invention, there is provided a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl] methoxy]propyl]adenine, comprising one or more of the following steps (a-c):
   a. reacting phenyl((R)-1-(6-amino-9H-purin-9-yl)propan-2-yloxy)methyl phosphonochloridate with 2-aminopropionic acid isopropyl ester or the hydrochloride salt thereof and a suitable chiral organic acid to obtain a diastereomeric organic acid addition salt of 9-[(R)-2-[[(R,S)-[[(S)-1(Isopropoxycarbonyl)ethyl]amino]phenoxyphosphinyl]methoxy]propyl]adenine; and/or b. crystallising a diastereomeric organic acid addition salt of 9-[(R)-2-[[(R,S)-[[(S)-1(Isopropoxycarbonyl)ethyl]amino]phenoxyphosphinyl]methoxy]propyl]adenine using a suitable solvent or mixture of solvents; and/or c. treating a diastereomeric organic acid addition salt of 9-[(R)-2-[[(R,S)-[[(S)-1(Isopropoxycarbonyl)ethyl]amino]phenoxyphosphinyl]methoxy]propyl]adenine with a suitable base; and optionally thereafter performing one or more of the following steps:

d. isolating 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine; and/or e. increasing the diastereomeric purity of the product so formed.

In one embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (a), (b) and (c) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (a), (b), (c) and (d) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (a), (b), (c), (d) and (e) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (a) and (b) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (a) and (c) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (b) and (c) disclosed herein.

In an alternative embodiment, the present invention provides a process for preparing 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine comprising steps (c) and (d) disclosed herein.

In the first step (step a) of a process of the present invention, phenyl((R)-1-(6-amino-9H-purin-9-yl)propan-2-yloxy)methyl phosphonochloridate (Formula II) is reacted with 2-amino-propionic acid isopropyl ester or the hydrochloride salt thereof (Formula III) and treated with a chiral organic acid to obtain a diastereomeric organic acid addition salt of 9-[(R)-2-[[(R,S)-[[(S)-1(Isopropoxycarbonyl)ethyl]amino]phenoxyphosphinyl]methoxy]propyl]adenine, i.e. a mixture of an organic acid addition salt of (9-[(R)-2-[[(S)-[[(S)-1-(Isopropoxycarbonyl)ethyl]amino]phenoxyphosphinyl]methoxy]propyl]adenine) and an organic acid addition salt of (9-[(R)-2-[[(R)-[[(S)-1(Isopropoxycarbonyl)ethyl]amino]phenoxyphosphinyl]methoxy]propyl]adenine).

The mixture may be racemic (50:50) or may contain a higher proportion of one diastereomeric salt relative to the other; for example, a higher proportion of (9-[(R)-2-[[(S)-[[(S)-1-(Isopropoxycarbonyl)ethyl]amino]phenoxyphosphinyl]methoxy]propyl]adenine) D-tartrate, such as 95%, relative to (9-[(R)-2-[[(R)-[[(S)-1(Isopropoxycarbonyl)ethyl]amino]phenoxyphosphinyl]methoxy]propyl]adenine) D-tartrate, such as 5%.

Preferably, 2-amino-propionic acid isopropyl ester hydrochloride is employed in the first step (step a) of a process of the present invention.

The chiral organic acid used in the first step (step a) of a process of present invention is most preferably D-tartaric acid or L-tartaric acid. Other suitable organic chiral acids which may be employed include, but are not limited to, di-p-anisoyl-D-tartaric acid, di-p-anisoyl-L-tartaric acid, di-benzoyl-D-tartaric acid, di-benzoyl-L-tartaric acid, di-p-tolyl-L-tartaric acid, di-p-tolyl-D-tartaric acid, diacetyl-L-tartaric acid, diacetyl-D-tartaric acid, R-mandelic acid, S-mandelic acid, D-malic acid and L-malic acid.

The reaction between phenyl((R)-1-(6-amino-9H-purin-9-yl)propan-2-yloxy)methyl phosphonochloridate (Formula II) and 2-amino-propionic acid isopropyl ester or the hydrochloride salt thereof (Formula III) is preferably carried out at a temperature in the range of from about 0 to about 5° C. The reaction is preferably performed in the presence of a suitable solvent, such as a polar aprotic solvent, more preferably a solvent selected from dichloromethane, ethyl acetate, tetrahydrofuran, acetonitrile, dimethyl formamide, toluene or any mixture thereof. The reaction is preferably performed in the presence of a suitable base, such as triethylamine.

In the second step (step b) of a process of the present invention, the diastereomeric acid addition salt of 9-[(R)-2-[[(R)-[[(S)-1(Isopropoxycarbonyl)ethyl]amino]phenoxyphosphinyl]methoxy]propyl]adenine or diastereomeric acid addition salt of 9-[(R)-2-[[(S)-[[(S)-1-(Isopropoxycarbonyl)ethyl]amino]phenoxyphosphinyl]methoxy]propyl]adenine is obtained by crystallisation using a suitable solvent or mixture of solvents. Typically, a mixture comprising an organic acid addition salt of (9-[(R)-2-[[(S)-[[(S)-1-(Isopropoxycarbonyl)ethyl]amino]phenoxyphosphinyl]methoxy]propyl]adenine) and an organic acid addition salt of (9-[(R)-2-[[(R)-[[(S)-1(Isopropoxycarbonyl)ethyl]amino]phenoxyphosphinyl]methoxy]propyl]adenine) is treated with a suitable solvent.

The mixture may be racemic (50:50) or may contain a higher proportion of one diastereomeric salt relative to the other; for example, a higher proportion of (9-[(R)-2-[[(S)-[[(S)-1-(Isopropoxycarbonyl)ethyl]amino]phenoxyphosphinyl]methoxy]propyl]adenine) D-tartrate, such as 95%, relative to (9-[(R)-2-[[(R)-[[(S)-1(Isopropoxycarbonyl)ethyl]amino]phenoxyphosphinyl]methoxy]propyl]adenine) D-tartrate, such as 5%.

The solvent mixture employed is preferably a mixture of water and one or more polar solvents. More preferably, the polar solvent is selected from methanol, ethanol, isopropanol, n-butanol, acetone and acetonitrile or any mixture thereof. Most preferably, the solvent is a mixture of water and acetonitrile. Crystallisation may be promoted by known methods, for example by heating a mixture containing organic acid addition salts of (9-[(R)-2-[[(S)-[[(S)-1-(Isopropoxycarbonyl)ethyl]amino]phenoxyphosphinyl]methoxy]propyl]adenine) and (9-[(R)-2-[[(R)-[[(S)-1(Isopropoxycarbonyl)ethyl]amino]phenoxyphosphinyl]methoxy]propyl]adenine) to a suitable temperature, such as from 50 to 100° C., preferably from 60 to 80° C., and thereafter cooling the mixture to effect precipitation.

When L-tartaric acid is used in the first step (step a) of a process of the present invention, a diastereomeric salt of 9-[(R)-2-[[(R)-[[(S)-1-(Isopropoxycarbonyl)ethyl]amino]phenoxyphosphinyl]methoxy]propyl]adenine with L-tartaric acid (Formula IVa) is obtained in crystalline form, while the filtrate contains the other diastereomer (RSS) salt.

When D-tartaric acid is used in the first step (step a) of a process of the present invention, a diastereomeric salt of 9-[(R)-2-[[(S)-[[(S)-1-(Isopropoxycarbonyl)ethyl]amino]phenoxyphosphinyl]methoxy]propyl]adenine with D-tartaric acid salt (Formula Va) is obtained in crystalline form, while the filtrate contains the other diastereomer (RRS) salt.

Preferably, the filtrate is further treated in order to recover the diastereomer which was not previously removed by precipitation. Preferably, the further treatment involves the conversion of the salt in the filtrate to its base using ammonia, or other similar bases, in water, followed by extraction and isolation of the base.

In the third step (step c) of a process of the present invention, the separated diastereomeric salt (e.g. a compound of Formula IVa or Formula Va) is treated with a suitable base to obtain pure 9-[(R)-2-[[(R)-[[(S)-1-(Isopropoxycarbonyl)ethyl]amino]phenoxyphosphinyl]methoxy]propyl]adenine (Formula Ia) or 9-[(R)-2-[[(S)-[[(S)-1-(Isopropoxycarbonyl)ethyl]amino]phenoxyphosphinyl]methoxy]propyl]adenine (Formula Ib) respectively.

The base used in the third step (step c) of a process of the present invention may be any suitable organic or inorganic base. The base may be selected from ammonia, sodium hydroxide, potassium hydroxide, sodium carbonate, potassium carbonate, ammonium bicarbonate, sodium bicarbonate, lithium hydroxide, lithium carbonate, triethylamine, diisopropylamine and the like. Preferably, the base is aqueous ammonia. The third step (c) of the process of the present invention is preferably performed in a suitable solvent. Most preferably, the solvent is a mixture of water and dichloromethane, toluene, tetrahydrofuran or dimethyl formamide.

Upon preparation, 9-[(R)-2-[[(R)-[[(S) 1(Isopropoxycarbonyl)ethyl]amino]phenoxyphosphinyl]methoxy]propyl]adenine and 9-[(R)-2-[[(S)-[[(S)-1-(Isopropoxycarbonyl)ethyl]amino]phenoxyphosphinyl]methoxy]propyl]adenine may be conveniently isolated using conventional methods known in the art. Exemplary isolation methods include such as filtration, vacuum distillation, crystallization and the like.

Upon isolation, the diastereomeric purity of 9-[(R)-2-[[(R)-[[(S) 1(Isopropoxycarbonyl)ethyl]amino]phenoxyphosphinyl]methoxy]propyl]adenine and 9-[(R)-2-[[(S)-[[(S)-1-(Isopropoxycarbonyl)ethyl]amino]phenoxyphosphinyl]methoxy]propyl]adenine may be increased using conventional methods known in the art. An exemplary enrichment method comprises slurrying 9-[(R)-2-[[(R)-[[(S) 1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine in one or more suitable solvents, such as a mixture of water and acetonitrile, with heating, followed by cooling and isolating the precipitate so formed.

The preferred processes of present invention (using L- or D-tartaric acid as a resolving agent) are depicted in general terms below in SCHEME I and SCHEME II.

SCHEME I: L-tartaric acid as resolving agent

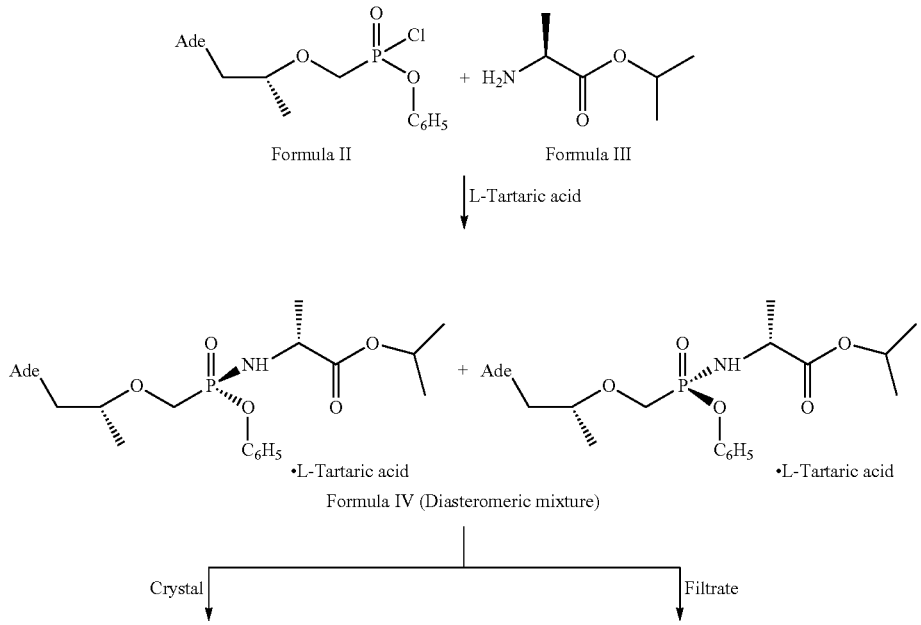

-continued
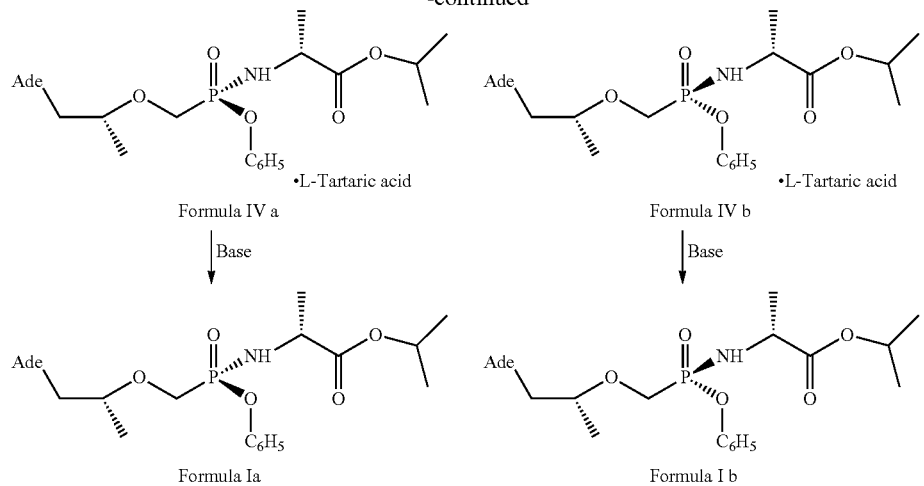
Wherein 'Ade' means Adenine
SCHEME II: D-tartaric acid as resolving agent
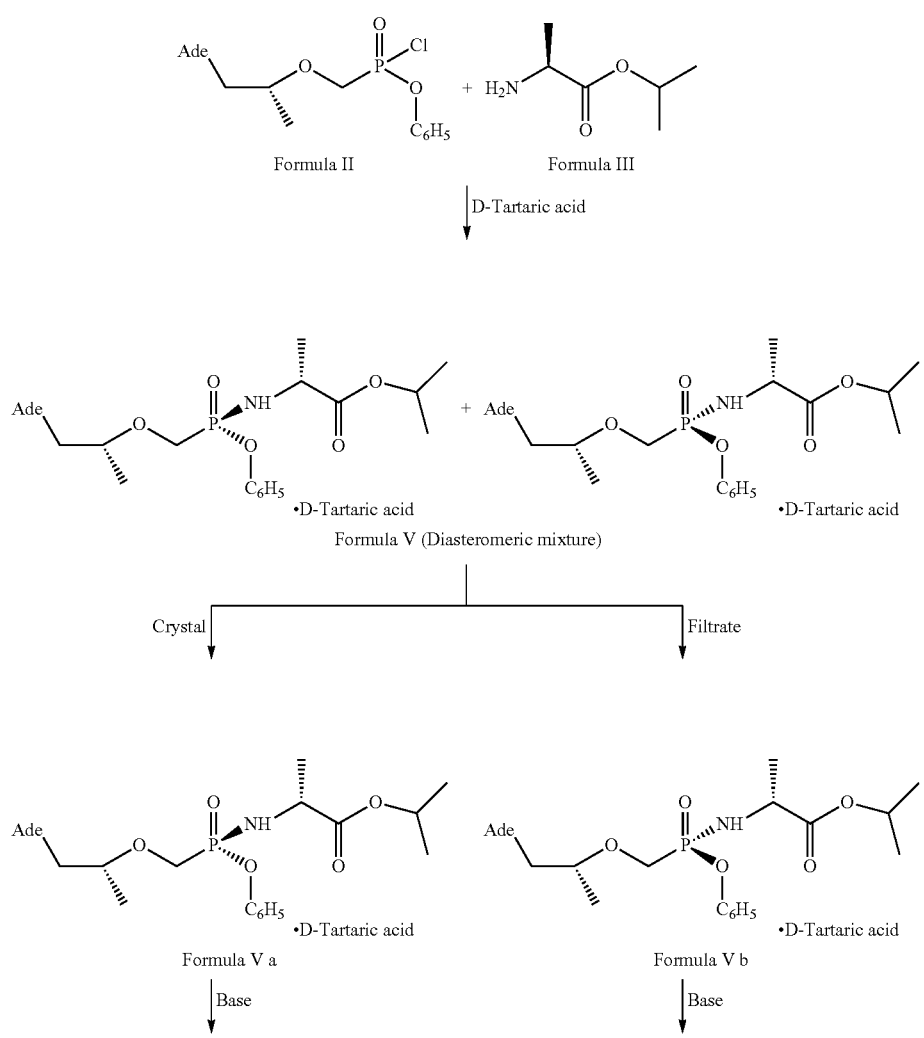

-continued

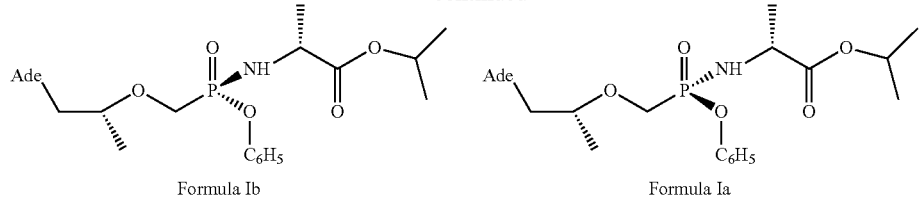

Formula Ib            Formula Ia

Wherein 'Ade' means Adenine

For the separation of diastereomers various resolving agents were tried, but surprisingly the inventors of the present invention found that highly efficient separation of diastereomers was achieved when D- or L-tartaric acid was used. The results of the experiments are as follows:

| Chiral Reagent | Chiral Purity |
| --- | --- |
| Di-p-anisoyl-D-tartaric acid | ≤50% |
| Di-p-anisoyl-L-tartaric acid | ≤50% |
| Di-benzoyl-D-tartaric acid | ≤50% |
| Di-benzoyl-L-tartaric acid | ≤50% |
| L-tartaric acid | >97% |
| D-tartaric acid | >97% |
| Di-p-tolyl-L-tartaric acid | ≤50% |
| Di-p-tolyl-D-tartaric acid | ≤50% |
| Diacetyl-L-tartaric acid | ≤50% |
| Diacetyl-D-tartaric acid | ≤50% |
| R-Mandelic acid | ≤50% |
| S-Mandelic acid | ≤50% |
| D-malic acid | ≤50% |
| L-malic acid | ≤50% |

The resolving agent that preferentially binds one of the diastereomer of the molecule to afford a species less soluble in the solvent media than the non-desired diastereomer is selected for the experiment. The salt that is formed is then separated and converted back to the free compound to lead to the pure desired diastereomer.

In the methods disclosed in WO200208241, in order to maintain the purity of ((R)-1-(6-amino-9H-purin-9-yl)propan-2-yloxy)methyl phosphonochloridate and L-alanine isopropyl ester the reaction between the two was carried out at −18° C. or −10° C. (as reported in the examples). While in the present invention due to the preferred use of L-alanine isopropyl ester hydrochloride instead of L-alanine isopropyl ester, the reaction with phenyl((R)-1-(6-amino-9H-purin-9-yl)propan-2-yloxy)methyl phosphonochloridate in the first step of the process can easily be carried out at a temperature in the range from about 0 to about 5° C. This is advantageous from an industrial standpoint i.e. when manufacturing on a large scale, as maintaining a very low (minus range) temperature during bulk production is not feasible and also increases the cost of production.

In another aspect of the present invention, optionally the separated 9-[(R)-2-[[(R)-[[(S)-1-(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine may be converted to the corresponding salt by reacting with a suitable acid, such as fumaric acid, lactic acid, malic acid, succinic acid, malonic acid, oxalic acid and the like. Preferably, the acid used is fumaric acid.

In another aspect of the present invention, there is provided 9-[(R)-2-[[(R)-[[(S)-1-(Isopropoxycarbonyl)ethyl]amino]phenoxyphosphinyl]methoxy]propyl]adenine (or the fumarate salt thereof), or 9-[(R)-2-[[(S)-[[(S)-1-(Isopropoxycarbonyl)ethyl]amino]phenoxyphosphinyl]methoxy]propyl]adenine (or the fumarate salt thereof), prepared according to a process of the present invention.

In yet another aspect of the present invention, there is provided a pharmaceutical composition comprising 9-[(R)-2-[[(R)-[[(S)-1-(Isopropoxycarbonyl)ethyl]amino]phenoxyphosphinyl]methoxy]propyl]adenine (or the fumarate salt thereof) or 9-[(R)-2-[[(S)-[[(S)-1-(Isopropoxycarbonyl)ethyl]amino]phenoxyphosphinyl]methoxy]propyl]adenine (or the fumarate salt thereof), prepared according to the process of the present invention, and one or more pharmaceutically acceptable excipients.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Separation of Diastereomers Using D-Tartaric Acid

Step 1—

Phenyl((R)-1-(6-amino-9H-purin-9-yl)propan-2-yloxy)methyl phosphonochloridate (15 gm, 0.041 mol) was slurried in toluene (100 ml) at 25-30° C. and cooled. L-alanine isopropyl ester hydrochloride (7.2 gm, 0.043 mol) and triethylamine was added. The reaction mass was stirred at 0-5° C. After completion of reaction, the reaction mass was quenched and solvent was distilled under vacuum. Dichloromethane was added and the layers were separated. Organic layer was collected and solvent was distilled. Acetonitrile (100 ml) and D-tartaric acid (6.2 gm, 0.413 mol) was added to the residue, contents heated to 70-80° C., cooled and filtered to obtain (9-[(R)-2-[[(R,S)-[[(S)-1-(Isopropoxycarbonyl)ethyl]amino]-phenoxy phosphinyl]methoxy]propyl]adenine)D-tartrate, a mixture of (9-[(R)-2-[[(S)-[[(S)-1-(Isopropoxycarbonyl)ethyl]amino]phenoxyphosphinyl]methoxy]propyl]adenine) D-tartrate and (9-[(R)-2-[[(R)-[[(S)-1(Isopropoxycarbonyl)ethyl]amino]phenoxyphosphinyl]methoxy]propyl]adenine) D-tartrate.

Yield=12 gm

Efficiency=(26.6%)

Step 2—

(9-[(R)-2-[[(R,S)-[[(S)-1-(Isopropoxycarbonyl)ethyl]amino]phenoxyphosphinyl]methoxy]propyl]adenine)D-tartrate (12 gm, 0.0108 mol) was slurried in mixture of water (100 ml) and acetonitrile (10 ml). The slurry was heated to 60-65° C., cooled and filtered to obtain (9-[(R)-2-[[(S)-[[(S)-

1-(Isopropoxycarbonyl)ethyl]amino]-phenoxyphosphinyl] methoxy]propyl]adenine) D-tartrate. The filtrate was collected.

Yield=6 gm, 95% (9-[(R)-2-[[(S)-[[(S)-1-(Isopropoxycarbonyl)ethyl]amino]phenoxyphosphinyl]methoxy]propyl] adenine) D-tartrate and 5% (9-[(R)-2-[[(R)-[[(S)-1-(Isopropoxycarbonyl)ethyl]amino]phenoxyphosphinyl] methoxy]propyl]adenine) D-tartrate.

1H NMR (500 MHz, DMSO, δ): 1.03 (d, 3H), 1.12 (m, 9H), 3.7-4.0 (m, 4H), 4.1 (dd, 1H), 4.2 (dd, 1H), 4.27 (s, 2H), 4.82 (m, 1H), 5.6 (t, 1H), 7.0 (d, 2H), 7.1 (t, 1H), 7.17 (s, 2H), 7.26 (t, 2H), 8.07 (s, 1H), 8.11 (s, 1H); $^{31}$P NMR (202.3 MHz, DMSO, δ): 22.7 (decoupled).

Step 3—

9-[(R)-2-[[(S)-[[(S)-1-(Isopropoxycarbonyl)ethyl]amino] phenoxyphosphinyl]methoxy]propyl]adenine D-tartrate (6 gm, 0.0054 mol) was slurried in dichloromethane (10 ml) and water (10 ml) and pH was adjusted to 8-9 using aqueous ammonia. The organic layer was collected and dichloromethane was distilled under vacuum. Water (10 ml) was added to the residue, heated to 55-60° C., cooled and filtered to obtain 9-[(R)-2-[[(S)-[[(S)-1-(Isopropoxycarbonyl)ethyl] amino]phenoxyphosphinyl]methoxy]propyl]adenine.

Yield=4.2 gm

Diastereomeric purity=99.5%,

Efficiency=81%

Step 4—

The pH of the filtrate containing (9-[(R)-2-[[(R)-[[(S)-1 (Isopropoxycarbonyl)ethyl]amino]phenoxyphosphinyl] methoxy]propyl]adenine) D-tartrate (the R-isomer 90% diastereomeric purity), from step 2, was adjusted to 8-9 pH using aqueous ammonia and extracted in dichloromethane. The organic layer was collected and dichloromethane was distilled under vacuum. To the residue, water (10 ml) was added and contents heated to 55-60° C., cooled and filtered to obtain 9-[(R)-2-[[(R)-[[(S)-1-(Isopropoxycarbonyl)ethyl] amino]-phenoxyphosphinyl]methoxy]propyl]adenine.

Yield=4.2 gm

Diastereomeric purity=99.3%

Example 2

Preparation of 9-[(R)-2-[[(S)-[[(S)-1-(Isopropoxycarbonyl)ethyl]amino]phenoxy phosphinyl] methoxy]propyl]adenine-D-tartrate 9-[(R)-2-[[(R,S)-[[(S)-1-(Isopropoxycarbonyl)ethyl] amino]phenoxyphosphinyl]methoxy]propyl]adenine (10 gm, 0.021 mol), prepared from any reported process, was dissolved in acetonitrile (100 ml) and treated with D-tartaric acid (4.1 gm, 0.027 mol) at 60-65° C. The reaction mixture was cooled and filtered to obtain 9-[(R)-2-[[(R,S)-[[(S)-1-(Isopropoxycarbonyl)ethyl]amino]-phenoxyphosphinyl] methoxy]propyl]adenine-D-tartrate.

The 9-[(R)-2-[[(R,S)-[[(S)-1-(Isopropoxycarbonyl)ethyl] amino]-phenoxyphosphinyl]methoxy]propyl]adenine-D-tartrate was then converted to 9-[(R)-2-[[(S)-[[(S)-1-(Isopropoxycarbonyl)ethyl]amino]-phenoxyphosphinyl] methoxy]propyl]adenine by following the process disclosed in Example 1.

Example 3

Separation of Diastereomers Using L-Tartaric Acid

Step 1—

Phenyl((R)-1-(6-amino-9H-purin-9-yl)propan-2-yloxy) methyl phosphonochloridate (20 gm, 0.055 mol) was slurried in toluene (130.5 ml). L-alanine isopropyl ester hydrochloride (9.6 gm, 0.0575 mol) was added followed by triethylamine. The reaction mass was stirred at 0-5° C. After completion of reaction, the mass was quenched and layers were separated. The organic layer was collected and solvent was distilled. Acetonitrile (130 ml) and L-tartaric acid (8.2 gm, 0.054 mol) was added to the residue, heated to 70-80° C., cooled and filtered to get (9-[(R)-2-[[(R,S)-[[(S)-1-(Isopropoxycarbonyl)ethyl]amino]phenoxyphosphinyl] methoxy]propyl]adenine) L-tartrate.

Yield=16 gm

Efficiency=26.2%

Step 2—

(9-[(R)-2-[[(R,S)-[[(S)-1-(Isopropoxycarbonyl)ethyl] amino]phenoxyphosphinyl]methoxy]propyl]adenine) L-tartrate (16 gm 0.0144 mol) was slurried in mixture of water (130 ml) and acetonitrile (1.3 ml). The slurry was heated at 60-65° C., cooled and filtered to get (9-[(R)-2-[[(R)-[[(S)-1-(Isopropoxycarbonyl)ethyl]amino]-phenoxyphosphinyl] methoxy]propyl]adenine) L-tartrate. The filtrate was collected.

Yield=8 gm, 95% of (9-[(R)-2-[[(R)-[[(S)-1-(Isopropoxycarbonyl)ethyl]amino]phenoxyphosphinyl]methoxy]propyl] adenine) L-tartrate and 5% of (9-[(R)-2-[[(S)-[[(S)-1-(Isopropoxycarbonyl)ethyl]amino]phenoxyphosphinyl] methoxy]propyl]adenine) L-tartrate.

$^1$H NMR (500 MHz, DMSO, δ): 1.03 (d, 3H), 1.11 (m, 9H), 3.7-4.0 (m, 4H), 4.1 (dd, 1H), 4.2 (dd, 1H), 4.29 (s, 2H), 4.82 (m, 1H), 5.46 (t, 1H), 7.1 (d, 2H), 7.1 (t, 1H), 7.16 (s, 2H), 7.31 (t, 2H), 8.09 (s, 1H), 8.11 (s, 1H); $^{31}$P NMR (202.3 MHz, DMSO, δ): 23.4 (decoupled).

Step 3—

9-[(R)-2-[[(R)-[[(S)-1-(Isopropoxycarbonyl)ethyl]amino] phenoxyphosphinyl]methoxy]propyl]adenine-L-tartrate (8 gm, 0.0072 mol) was slurried in dichloromethane (130.5 ml) and water (13.5 ml). The pH of slurry was adjusted to 8-9 using aqueous ammonia. The layers were separated and organic solvent was distilled. Water (13.5 ml) was added to the residue, heated at 55-60° C., cooled and filtered to obtain 9-[(R)-2-[[(R)-[[(S)-1-(Isopropoxycarbonyl)ethyl]amino] phenoxyphosphinyl]methoxy]propyl]adenine.

Yield=5.6 gm

Diastereomeric purity=99.4%

Efficiency=81%

Step 4—

Filtrate which contains (9-[(R)-2-[[(S)-[[(S)-1-(Isopropoxycarbonyl)ethyl]amino]phenoxyphosphinyl] methoxy]propyl]adenine) L-tartrate (the S-isomer 90% diastereomeric purity), from step 2, was adjusted to 8-9 pH using liquor ammonia and extracted in dichloromethane. The organic solvent was distilled and water (13.5 ml) was added. The contents were heated, cooled and filtered to obtain 9-[(R)-2-[[(S)-[[(S)-1-(Isopropoxycarbonyl)ethyl] amino]phenoxyphosphinyl]methoxy]propyl]adenine.

Yield=5.6 gm

Diastereomeric purity=99.2%

Example 4

Preparation of 9-[(R)-2-[[(R)-[[(S)-1-(Isopropoxycarbonyl)ethyl]amino]phenoxyphosphinyl]methoxy]propyl]adenine-L-tartrate 9-[(R)-2-[[(R,S)-[[(S)-1-(Isopropoxycarbonyl)ethyl]amino]phenoxyphosphinyl]methoxy]propyl]adenine, prepared from any reported process, was dissolved in acetonitrile and treated with L-tartaric acid at 60-65° C. The reaction mixture was cooled and filtered to obtain 9-[(R)-2-[[(R,S)[[(S)-1-(Isopropoxycarbonyl)ethyl]amino]-phenoxyphosphinyl]methoxy]propyl]adenine-L-tartrate.

The 9-[(R)-2-[[(R,S)-[[(S)-1-(Isopropoxycarbonyl)ethyl]amino]-phenoxyphosphinyl]methoxy]propyl]adenine-L-tartrate was then converted to 9-[(R)-2-[[(R)-[[(S)-1-(Isopropoxycarbonyl)ethyl]amino]-phenoxyphosphinyl]methoxy]propyl]adenine by following the process disclosed in Example 3.

Example 5

Preparation of 9-[(R)-2-[[(S)-[[(S)-1-(Isopropoxycarbonyl)ethyl]amino]phenoxy phosphinyl]methoxy]propyl]adenine fumarate or 9-[(R)-2-[[(R)-[[(S)-1-(Isopropoxycarbonyl)ethyl]amino]-phenoxyphosphinyl]methoxy]propyl]adenine fumarate The 9-[(R)-2-[[(S)-[[(S)-1-(Isopropoxycarbonyl)ethyl]amino]phenoxyphosphinyl]methoxy]propyl]adenine, obtained from Example 1 or 2, was treated with fumaric acid to yield 9-[(R)-2-[[(S)-[[(S)-1-(Isopropoxycarbonyl)ethyl]amino]phenoxyphosphinyl]methoxy]propyl]adenine fumarate.

Similarly, the 9-[(R)-2-[[(R)-[[(S)-1(Isopropoxycarbonyl)ethyl]amino]phenoxyphosphinyl]methoxy]propyl]adenine, obtained from Example 3 or 4, was treated with fumaric acid to yield the 9-[(R)-2-[[(R)-[[(S)-1-(Isopropoxycarbonyl)ethyl]amino]-phenoxyphosphinyl]methoxy]propyl]adenine fumarate salt.

Example 6

Enrichment of the Diasteriomeric Purity of (9-[(R)-2-[[(S)-[[(S)-1-(Isopropoxycarbonyl)ethyl]amino]-phenoxyphosphinyl]methoxy]propyl]adenine) D-tartrate (9-[(R)-2-[[(S)-[[(S)-1-(Isopropoxycarbonyl)ethyl]amino]phenoxyphosphinyl]methoxy]propyl]adenine)D-tartrate (12 gm, 0.0108 mol) having a diasteriomeric purity of 70% (prepared in example 1-step 2) was slurried in a mixture of water (60 ml) and acetonitrile (6 ml). The slurry was heated to 60-65° C., cooled and filtered to obtain (9-[(R)-2-[[(S)-[[(S)-1-(Isopropoxycarbonyl)ethyl]amino]-phenoxyphosphinyl]methoxy]propyl]adenine) D-tartrate with a 90% diasteriomeric purity.

The above compound was then further slurried in a mixture of water (60 ml) and acetonitrile (6 ml). The slurry was heated to 60-65° C., cooled and filtered to obtain (9-[(R)-2-[[(S)-[[(S)-1-(Isopropoxycarbonyl)ethyl]amino]-phenoxyphosphinyl]methoxy]propyl]adenine) D-tartrate with a 99.5% diasteriomeric purity.

This same procedure could be repeated with the compound obtained in example 3, step 4 but in this case the solvent would preferably be acetonitrile (instead of a mixture of solvents).

Example 7

Isolation of (9-[(R)-2-[[(R)-[[(S)-1-(Isopropoxycarbonyl)ethyl]amino]phenoxy phosphinyl]methoxy]propyl]adenine) L-tartrate without Crystallization Phenyl((R)-1-(6-amino-9H-purin-9-yl)propan-2-yloxy)methyl phosphonochloridate (10 gm, 0.0255 mol) was slurried in toluene (70 ml). L-alanine isopropyl ester hydrochloride (4.75 gm, 0.02585 mol) was added followed by triethylamine. The reaction mass was stirred at 0-5° C. After completion of the reaction, the mass was quenched and layers were separated. The organic layer was collected and the solvent was distilled. Acetonitrile (70 ml), water (10 ml) and L-tartaric acid (4.1 gm, 0.0274 mol) was added to the residue, heated to 70-80° C., cooled and filtered to get 95% of (9-[(R)-2-[[(R)-[[(S)-1-(Isopropoxycarbonyl)ethyl]amino]phenoxy phosphinyl]methoxy]propyl]adenine) L-tartrate and 5% of (9-[(R)-2-[[(S)-[[(S)-1-(Isopropoxycarbonyl)ethyl]amino]phenoxyphosphinyl]methoxy]propyl]adenine) L-tartrate.
Yield=4.5 gm
Efficiency=28%

Example 8

Isolation of (9-[(R)-2-[[(S)-[[(S)-1-(Isopropoxycarbonyl)ethyl]amino]phenoxy phosphinyl]methoxy]propyl]adenine) L-tartrate without Crystallization Phenyl((R)-1-(6-amino-9H-purin-9-yl)propan-2-yloxy)methyl phosphonochloridate (10 gm, 0.0255 mol) was slurried in toluene (70 ml). L-alanine isopropyl ester hydrochloride (4.75 gm, 0.02585 mol) was added followed by triethylamine. The reaction mass was stirred at 0-5° C. After completion of the reaction, the mass was quenched and the layers were separated. The organic layer was collected and the solvent was distilled. Acetonitrile (70 ml), water (10 ml) and D-tartaric acid (4.1 gm, 0.0274 mol) were added to the residue, heated to 70-80° C., cooled and filtered to obtain 95% of (9-[(R)-2-[[(S)-[[(S)-1-(Isopropoxycarbonyl)ethyl]amino]phenoxy phosphinyl]methoxy]propyl]adenine) D-tartrate and 5% of (9-[(R)-2-[[(R)-[[(S)-1-(Isopropoxycarbonyl)ethyl]amino]phenoxy phosphinyl]methoxy]propyl]adenine) D-tartrate.
Yield=4 gm
Efficiency=26%

The invention claimed is:
1. A process for preparing 9-[(R)-2-[[(R)-[[(S)-1-(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine, comprising steps (a), (b), (c) and (d):
  a. reacting phenyl((R)-1-(6-amino-9H-purin-9-yl)propan-2-yloxy)methyl phosphonochloridate with 2-aminopropionic acid isopropyl ester or the hydrochloride salt thereof and a chiral organic acid to obtain a diastereomeric organic acid addition salt of 9-[(R)-2-[[(R,S)-[[(S)-1(Isopropoxycarbonyl)ethyl]amino]phenoxy- phosphinyl]methoxy]propyl]adenine wherein the chiral organic acid employed is L-tartaric acid or D-tartaric acid; and b. crystallising the diastereomeric organic acid addition salt of 9-[(R)-2-[[(R,S)-[[(S)-1(Isopropoxycarbonyl)ethyl]amino]phenoxyphosphinyl]methoxy]propyl]adenine using a solvent or mixture of solvents; and c. treating the diastereomeric organic acid addition salt of 9-[(R)-2-[[(R,S)-[[(S)-1(Isopropoxycarbonyl)ethyl]amino]phenoxyphosphinyl]methoxy]propyl]adenine with a base; and:

d. isolating 9-[(R)-2-[[(R)-[[(S)-1(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine.

2. The process according to claim 1, wherein step (a) comprises the use of 2-amino-propionic acid isopropyl ester hydrochloride.

3. The process according to claim 1, wherein step (a) is performed in one or more polar aprotic solvents.

4. The process according to claim 3, wherein the polar aprotic solvent is one or more solvents selected from the group consisting of dichloromethane, ethyl acetate, tetrahydrofuran, acetonitrile, dimethyl formamide and toluene.

5. The process according to claim 1, wherein step (a) is performed at a temperature in the range from 0 to 5° C.

6. The process according to claim 1, wherein step (b) is performed in a mixture of water and one or more polar solvents.

7. The process according to claim 6, wherein the polar solvent is one or more solvents selected from the group consisting of methanol, ethanol, isopropanol, n-butanol, acetone and acetonitrile.

8. The process according to claim 6, wherein step (b) is performed in water and acetonitrile.

9. The process according to claim 1, wherein the base employed in step (c) is aqueous ammonia.

10. The process according to claim 1, wherein step (c) is performed in a mixture of water and dichloromethane, toluene, tetrahydrofuran or dimethyl formamide.

11. The process according to claim 1, wherein after step (d), further comprising the step of converting separated 9-[(R)-2-[[(R)-[[(S)-1-(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine to an acid addition salt by treatment with an acid.

12. The process according to claim 11, wherein the acid is fumaric acid.

13. A process for the separation of diastereomers of 9-[(R)-2-[[(R,S)-[[(S)-1-(Isopropoxycarbonyl)ethyl] amino] phenoxyphosphinyl]methoxy]propyl]adenine comprising the steps (a), (b), (c), (d) and (e) of:

a. reacting phenyl((R)-1-(6-amino-9H-purin-9-yl)propan-2-yloxy)methyl phosphonochloridate with 2-amino-propionic acid isopropyl ester or the hydrochloride salt thereof and a chiral organic acid to obtain a diastereomeric organic acid addition salt of 9-[(R)-2-[[(R,S)-[[(S)-1(Isopropoxycarbonyl)ethyl]amino]phenoxyphosphinyl]methoxy]propyl]adenine wherein the chiral organic acid is L-tartaric acid or D-tartaric acid;

b. crystallising the diastereomeric organic acid addition salt of 9-[(R)-2-[[(R,S)-[[(S)-1(Isopropoxycarbonyl)ethyl]amino]phenoxyphosphinyl]methoxy]propyl]adenine from the reaction mixture of step (a) using a solvent or mixture of solvents; and c. treating the diastereomeric organic acid addition salt of 9-[(R)-2-[[(R,S)-[[(S)-1(Isopropoxycarbonyl)ethyl]amino]phenoxyphosphinyl]methoxy]propyl]adenine from the reaction mixture of step (b) with a base;

d. isolating the product so formed; and e. increasing the diastereomeric purity of the product so formed.

14. The process according to claim 13, wherein step (a) comprises the use of 2-amino-propionic acid isopropyl ester hydrochloride.

15. The process according to claim 13, wherein step (a) is performed in one or more polar aprotic solvents.

16. The process according to claim 15, wherein the polar aprotic solvent is one or more solvents selected from the group consisting of dichloromethane, ethyl acetate, tetrahydrofuran, acetonitrile, dimethyl formamide and toluene.

17. The process according to claim 13, wherein step (a) is performed at a temperature in the range from 0 to 5° C.

18. The process according to claim 13, wherein step (b) is performed in a mixture of water and one or more polar solvents.

19. The process according to claim 18, wherein the polar solvent is one or more solvents selected from the group consisting of methanol, ethanol, isopropanol, n-butanol, acetone and acetonitrile.

20. The process according to claim 18, wherein step (b) is performed in water and acetonitrile.

21. The process according to claim 13, wherein the base employed in step (c) is aqueous ammonia.

22. The process according to claim 13, wherein step (c) is performed in a mixture of water and dichloromethane, toluene, tetrahydrofuran or dimethyl formamide.

23. The process according to claim 13, further comprising the step of converting separated 9-[(R)-2-[[(R)-[[(S)-1-(Isopropoxycarbonyl)ethyl]amino]phenoxyphosphinyl]methoxy]propyl]adenine or 9-[(R)-2-[[(S)-[[(S)-1-(Isopropoxycarbonyl)ethyl]amino]phenoxyphosphinyl]methoxy]propyl]adenine to an acid addition salt by treatment with an acid.

24. The process according to claim 23, wherein the acid is fumaric acid.

* * * * *